(12) United States Patent
Chang et al.

(10) Patent No.: US 9,044,526 B2
(45) Date of Patent: Jun. 2, 2015

(54) MEDICAL PRODUCT CONTAINING ACTIVE COMPONENT OF PROPOLIS OR GRAPEFRUIT SEED EXTRACT AND MANUFACTURING METHOD THEREOF

(75) Inventors: Jeong Ho Chang, Gwangmyeong-si (KR); Hye Sun Lee, Seoul (KR); Jin Hyung Lee, Hwaseong-si (KR)

(73) Assignee: Korea Institute of Ceramic Engineering and Technology, Seoul (KR)

( * ) Notice: Subject to any disclaimer, the term of this patent is extended or adjusted under 35 U.S.C. 154(b) by 134 days.

(21) Appl. No.: 13/348,751

(22) Filed: Jan. 12, 2012

(65) Prior Publication Data

US 2013/0129808 A1 May 23, 2013

(30) Foreign Application Priority Data

Nov. 23, 2011 (KR) .......................... 10-2011-0122973

(51) Int. Cl.
| | |
|---|---|
| *A61K 9/70* | (2006.01) |
| *A61K 31/216* | (2006.01) |
| *A61K 31/353* | (2006.01) |
| *A61K 36/752* | (2006.01) |
| *A61P 29/00* | (2006.01) |
| *A61P 31/04* | (2006.01) |
| *A61L 15/46* | (2006.01) |
| *A61L 15/40* | (2006.01) |
| *C07D 311/30* | (2006.01) |

(52) U.S. Cl.
CPC ............... *A61L 15/46* (2013.01); *A61K 36/752* (2013.01); *A61K 31/216* (2013.01); *A61K 31/353* (2013.01); *A61L 15/40* (2013.01); *A61L 2300/30* (2013.01); *A61L 2300/404* (2013.01); *C07D 311/30* (2013.01)

(58) Field of Classification Search
None
See application file for complete search history.

(56) References Cited

U.S. PATENT DOCUMENTS

| 4,382,886 | A | * | 5/1983 | Sosnowski | .................... | 530/200 |
| 2005/0123619 | A1 | * | 6/2005 | Farrell | .......................... | 424/526 |

OTHER PUBLICATIONS

Houghton et al., Phytochemical Analysis, 1995, 6, 207-210.*
Bankova et al., Z. Naturforsch, 2002, 530-533.*
M. Viuda-Martos et al., "Functional Properties of Honey, Propolis, and Royal Jelly", Journal of Food Science, vol. 73, Nr. 9, 2008, pp. 117-124, Institute of Food Technologists.

* cited by examiner

*Primary Examiner* — Kyle Purdy
(74) *Attorney, Agent, or Firm* — LRK Patent Law Firm

(57) ABSTRACT

A medical product containing either an active ingredient of propolis which is a natural antibiotic or a grapefruit seed extract, and a manufacturing method thereof are provided. The medical product is impregnated with a solution of CAPE (caffeic acid phenethyl ester) or pinocembrin, which is an active ingredient of propolis having antibacterial effects, to increase the antibacterial activity of the medical product due to antibacterial compounds contained in the active component, or the medical product is impregnated with a solution of a grapefruit seed extract such that the extract can exhibit antibacterial activity in the medical product.

1 Claim, 16 Drawing Sheets

Pinocembrin

MEDICAL PRODUCT CONTAINING ACTIVE COMPONENT OF PROPOLIS OR GRAPEFRUIT SEED EXTRACT AND MANUFACTURING METHOD THEREOF

CROSS REFERENCE TO RELATED APPLICATION

This application claims the benefit under 35 U.S.C. 119(a) of Korean Patent Application No. 10-2011-0122973, filed on Nov. 23, 2011, the disclosure of which is incorporated by reference in its entirety for all purposes.

BACKGROUND OF THE INVENTION

1. Field of the Invention

The present invention relates to a medical product, and more particularly to a medical product containing either an active ingredient of propolis which is a natural antibiotic or a grapefruit seed extract, and a manufacturing method thereof, in which the medical product is impregnated with a solution of CAPE (caffeic acid phenethyl ester) or pinocembrin, which is an active ingredient of propolis having antibacterial effects, to increase the antibacterial activity of the medical product due to antibacterial compounds contained in the active component, or in which the medical product is impregnated with a solution of a grapefruit seed extract such that the extract can exhibit antibacterial activity in the medical product.

2. Description of the Prior Art

A biomedical material (biomaterial) is a material that is used for the diagnosis or treatment of disease or to replace body tissue damaged due to disease or an accident. The requirements of the biomaterial include excellent biocompatibility, chemical stability, flexibility, durability, heat resistance, anti-aging activity, formability and processability, as well as low production costs.

Naringin that is one component of a grapefruit seed extract is a kind of flavonoid known as vitamin P having antibacterial effects. It is found mainly in the seed of ripe grapefruits and is bitter in taste. It has a molecular formula of $C_{27}H_{32}O_{14}2H_2O$ and a chemical formula represented by the following formula 1:

[Formula 1]

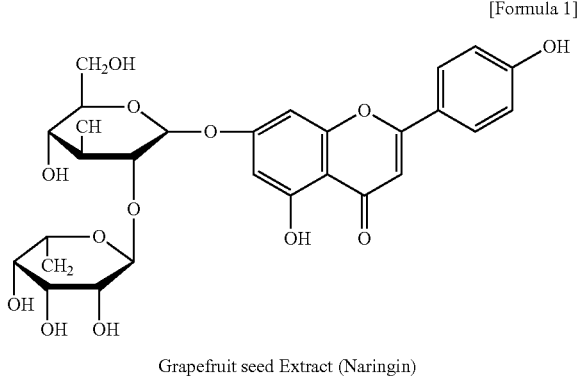

Grapefruit seed Extract (Naringin)

With respect to its main functions, naringin has a bacteriostatic effect of arresting the growth of microorganisms and an antibacterial effect of killing microorganisms. Also, naringin is a strong natural antioxidant having an effect superior to lipid-soluble tocopherol in food. Particularly, it is water-soluble, and thus is used in a wide range of applications and is nontoxic even when it is taken in excessive amounts.

Meanwhile, propolis is known to contain about 149 compounds and about 22 minerals. The main component thereof is comprised of 50% resin, 30% beeswax, 10% oiliness component such as refined oil, 5% pollen and 5% organic and minerals.

Nowadays, men and women of all ages suffer from various diseases, including nasitis, atopy, ozena, cancer, gastroenteric disorders and the like, due to a decrease in immunity caused by a contaminated environment and foods containing various harmful substances, and many people prefer to use the immune-enhancing effect of propolis, particularly the effect of flavonoid contained in propolis. Most current antibiotics are effective against only some bacteria and have problems in that they reduce the immunity of the human body and cause side effects and tolerance. However, propolis extracted from honeycombs overcome this limitation of antibiotics and directly kill almost all germs (viruses, bacteria, and fungi). In addition, it is a natural component, and thus does not cause tolerance and side effects and increases the immunity of the human body. Also, in the 5th International Propolis Symposium in May, 1980, Dr. Bent Havesteen at Keele University, Germany announced that more than 18 flavonoids have an excellent defensive power against viruses because the flavonoids act as a defense wall role against germs. Also, it was announced that the defense wall debilitates germs and viruses and create immunity effect, and flavonoid has been reported to be the most important substance in representing the biological function of propolis in the academic world.

A grapefruit seed extract that is used in the present invention has antibacterial activity. In addition, CAPE (caffeic acid phenethyl ester) and pinocembrin, which are the active components of propolis, are flavonoid components known as vitamin P and are known to show antibacterial and anti-inflammatory activities in propolis. CAPE has a molecular formula of $C_{17}H_{16}O_4$, and pinocembrin has a molecular formula of $C_{15}H_{12}O_4$, and these active components have chemical structures represented by the following formulas 2(a) and 2(b), respectively:

[Formula 2]

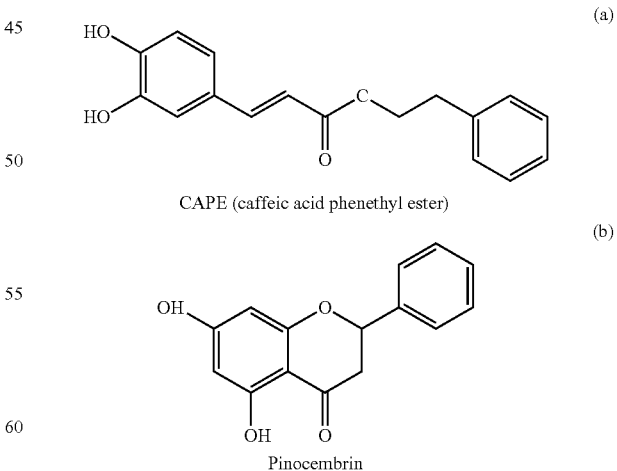

(a) CAPE (caffeic acid phenethyl ester)

(b) Pinocembrin

With respect to their main functions, CAPE and pinocembrin have antibacterial, antifungal and antiviral effects in the human body. Also, CAPE and pinocembrin inhibit the secretion of proinflammatory enzymes to inhibit the occurrence of inflammation. Particularly, they are water-soluble, and thus are used in a wide range of applications and are nontoxic even when they are taken in large amounts.

The principle of anti-inflammatory action of CAPE and pinocembrin will now be briefly described. In a process in which inflammation occurs, if the human body becomes acidic, waste matter accumulates in the body and around cells, and the cells start to be lysed such that the cell membrane and the waste are burned. As a result, cytotoxic substances such as leukotriene (LT) and prostaglandin (PG) which cause inflammatory responses such as fever and pain. Herein, in order to make cytotoxic substances such as proinflammatory LT and PG, enzymes such as lipoxygenase and cyclooxygenase are required. The reason why the active components (CAPE and pinocembrin) of propolis have a strong effect against inflammation is because these active components inhibit the two enzymes, lipoxygenase and cyclooxygenase, which produce the cytotoxic substances (LT and PG) causing inflammation.

The reason why propolis has a strong inflammatory effect compared to anti-inflammatory agents is because the anti-inflammatory agents inhibit only cyclooxygenase among the two enzymes during the production of the cytotoxic substances causing inflammation, whereas propolis inhibits the two enzymes. Thus, propolis can be regarded as an excellent inflammation-treating agent that has a strong effect on the inhibition of inflammation and causes no side effects.

Also, CAPE and pinocembrin act to inhibit the growth of malignant cells and repair cells damaged by carcinogenic substances.

The present inventor has applied CAPE and pinocembrin, which are the active components of propolis having various functions as described above, to a medical product, and has also applied a natural grapefruit seed extract to a medical product. As a result, the present inventor has developed a medical product which has antibacterial and anti-inflammatory activities and at the same time, does not cause the problem of nanoparticles remaining in vivo, and a manufacturing method thereof.

SUMMARY OF THE INVENTION

It is an object of the present invention to provide a medical product which contains an active component of propolis having antibacterial and inflammatory effects and a grapefruit seed extract which is a natural antibacterial material, so as to be able to prevent the occurrence of inflammation after surgery, thereby solving the problems occurring in existing medical products, and a manufacturing method thereof.

In accordance with a preferred embodiment of the present invention, there is provided a medical product containing a grapefruit seed extract or an active component of propolis.

In a preferred embodiment, the active component of the propolis may be CAPE (caffeic acid phenethyl ester) or pinocembrin.

In a preferred embodiment of the present invention, the medical product may be an absorbent cotton wool, a bandage, a cotton gauze or a cotton wool swab.

In accordance with another preferred embodiment of the present invention, there is provided a method for manufacturing a medical product, the method comprising impregnating a multifilament for a medical product with a methanol solution of a grapefruit seed extract and CAPE (caffeic acid phenethyl ester) or pinocembrin which is an active component of propolis, in which the concentration of the grapefruit seed extract and the active component of propolis is 500-3000 ppm.

In a preferred embodiment of the present invention, the medical product may be an absorbent cotton wool, a bandage, a cotton gauze or a cotton wool swab.

BRIEF DESCRIPTION OF THE DRAWINGS

The above and other objects, features and advantages of the present invention will be more clearly understood from, the following detailed description taken in conjunction with the accompanying drawing, in which.

DETAILED DESCRIPTION OF THE INVENTION

Figure 1:
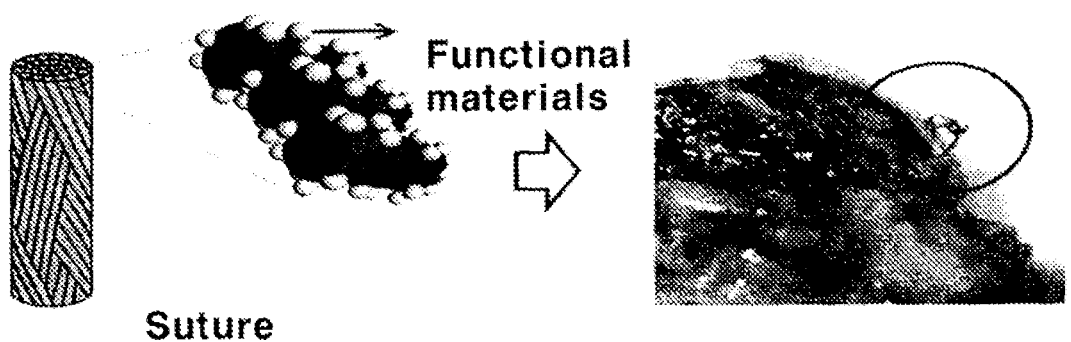
FIG. 1 is an image showing the use of a grapefruit seed extract and an active ingredient of propolis according to the present invention.

Hereinafter, a medical product containing a grapefruit seed extract and an active component of propolis according to the present invention and a manufacturing method thereof will be described in detail with reference to the accompanying drawings.

An antibacterial and anti-inflammatory product for medical use according to the present invention contains a grapefruit seed extract and CAPE or pinocembrin which is the active component of propolis.

CAPE or pinocembrin which is the active component of propolis is a kind of flavonoid in propolis.

CAPE and pinocembrin used in the following examples was purchased from Sigma Aldrich.

The grapefruit seed extract used in the following examples was df-100 purchased from FA Bank Co.

A biodegradable multifilament for the medical product is likely to be absorbed and degraded in vivo, and thus when it is exposed to water for a long time, it is degraded as the strength thereof is decreased. For this reason, methanol having a high degree of evaporation is preferably used to minimize the reaction of the multifilament with water.

Also, the medical product is preferably in the form of a multifilament. In addition, the medical product may further contain calcium stearate as a coating agent.

The multifilament is easy to proliferate with bacteria between the filaments compared to a monofilament. For this reason, when antibacterial activity is imparted to the multifilament according to the present invention, the proliferation of bacteria in the multifilament can be inhibited. In addition, because the multifilament contains the grapefruit seed extract and the active components (CAPE and pinocembrin) of propolis, which have antibacterial and anti-inflammatory functions, it can increase antibacterial activity and reduce the cause of infection which can occur during surgery. In addition, in order to make up for the rough surface of the suture and the parasitic space of bacteria, the coating agent such as calcium stearate may be used.

Meanwhile, the method for manufacturing the medical antibacterial product comprises the steps of: i) preparing a multifilament for a medical product (see Korean Patent Application No. 10-2009-0121725); ii) impregnating the prepared multifilament with a solution of a grapefruit seed extract and CAPE or pinocembrin which is the active component of propolis; and iii) examining the antibacterial and anti-inflammatory activities of the prepared medical product.

Also, the present invention provides a method for manufacturing a medical product, the method comprising impregnating a multifilament for a medical product with a methanol solution of a grapefruit seed extract and CAPE (caffeic acid phenethyl ester) or pinocembrin which is an active component of propolis, in which the concentration of the grapefruit seed extract and the active component of propolis is 500-3000 ppm. If the concentration of the active ingredient is less than 500 ppm, the medical product will have insufficient antibacterial activity, and if the concentration is more than 3000 ppm, the solubility of the active ingredient will be insufficient.

FIG. 1 is an image showing the use of the grapefruit seed extract and CAPE (the active component of propolis) according to the present invention. From FIG. 1, a method of using the grapefruit seed extract and CAPE can be seen.

Figure 2:
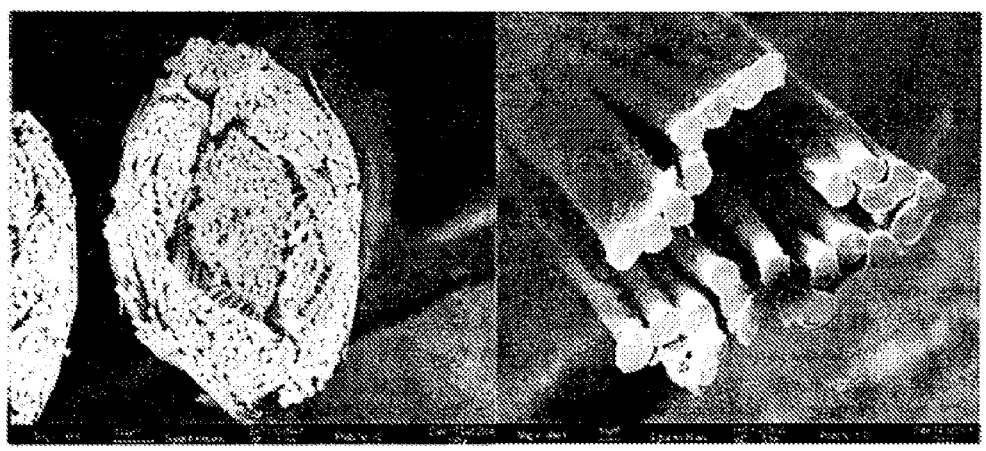
FIG. 2 is a FE-SEM photograph of a multifilament for a medical product according to one embodiment of the present invention.

FIG. 2 is an FE-SEM photograph of a multifilament for a medical product according to one embodiment of the present invention. Herein, the multifilament was prepared by spinning selected polymers at various composition ratios under the same conditions, comparing the physical properties between the composition ratios to select the optimal polymer composition ratio, and spinning the selected composition using a multifilament spinning machine under various spinning conditions, thus preparing a multifilament having excellent handling and knot stability.

The prepared multifilament was tested using a conjugate spinning machine at various polymer composition ratios, thus preparing the optimal conjugated multifilament.

Figure 3:
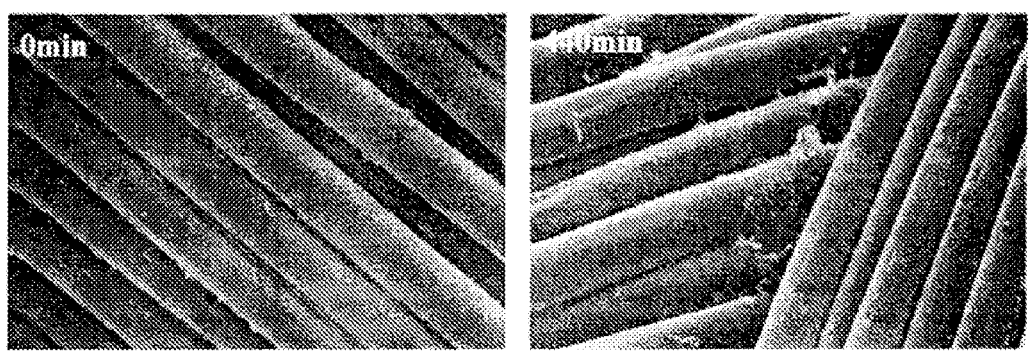
FIG. 3 is a set of SEM photographs showing the change of a multifilament for a medical product in a solution of a grapefruit seed extract and an active component of propolis as a function of time.

FIG. 3 is a set of SEM photographs taken after placing 1 g of the above-prepared multifilament with 30 ml of a methanol solution containing 1000 ppm of the grapefruit seed extract and CAPE or pinocembrin (the active component of propolis) and impregnating the multifilament with the methanol solution at 6-hr-intervals until the solution is no longer absorbed into the multifilament. FIG. 3 shows the multifilament before and after immersion in the solution having antibacterial and anti-inflammatory activities.

As can be seen in the figures, there is little or no change in the thickness of the multifilament which contains the grapefruit seed extract and the active component of propolis. This suggests that the multifilament can be conveniently used.

Hereinafter, examples of the present invention will be described in detail. It is to be understood, however, that these examples are for illustrative purposes and are not intended to limit the scope of the present invention.

EXAMPLE 1

Preparation of PGLA (poly(glycolide-co-L-lactide)

The multifilament used in the following examples was prepared through four processes in the following manner. First, poly-glycolide and lactide were melted to make a gel which was then mixed with a pigment. Herein, the process of mixing the gel with the pigment was carried out in a separate melting/mixing tank.

Then, the melted material was subjected to the following sequential processes: an extrusion process in which the melted material was pressurized through pressure chambers and extruded by alternately opening the valves provided in the pressure chambers; a spinning process in which the material supplied from the pressure chamber was strongly extruded in the form of thread though a spinneret; and a stretching process in which the spun thread was stretched using a stretching machine, thus increasing the tensile strength and elasticity of the thread.

This method for preparing the multifilament is based on the preparation method disclosed in Korean Patent Application No. 10-2009-0121725.

Figure 9:
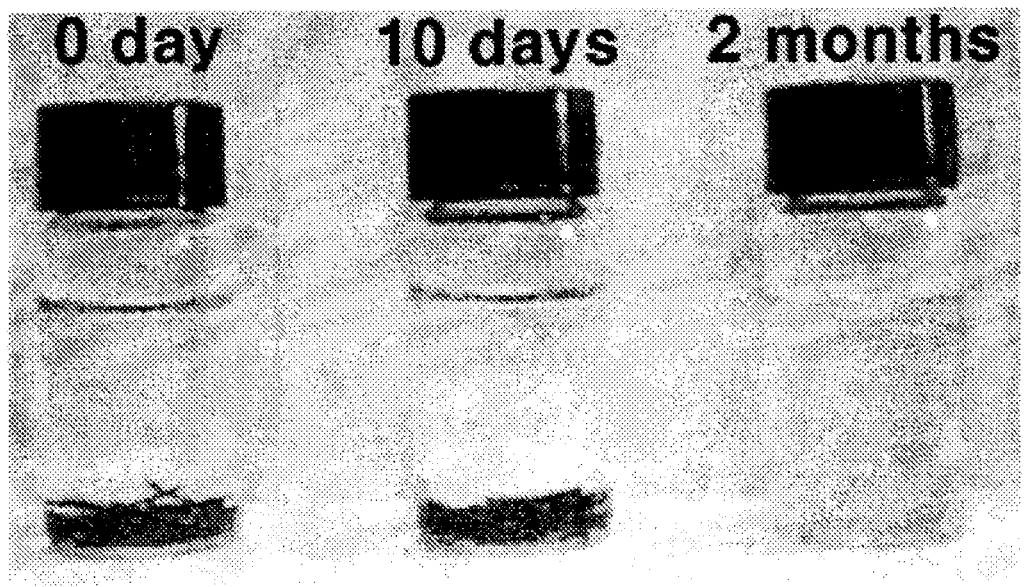
FIG. 9 shows the results of measuring the degradation of a multifilament (for a medical product) containing a grapefruit seed extract and an active component of propolis according to one embodiment of the present invention.

FIG. 9 is a photograph showing the results of observing the degradation behavior of 0.1 g of the PGLA multifilament in PBS solution (pH7.4; similar to the human body) for 0 day, 10 days and 2 months. As can be seen in FIG. 2, the degradation of the multifilament was significantly rapid. This suggests that the residence time of the multifilament in the human body is short such that second infection caused by the multifilament decreases. Also, it can be seen that the grapefruit seed extract and CAPE or pinocembrin which is the active component of propolis have no effect on the degradation of the multifilament.

EXAMPLE 2

Preparation of a Solution of a Grapefruit Seed Extract and CAPE or Pinocembrin which is the Active Component of Propolis A solution containing 1000 ppm of a grapefruit seed extract and CAPE or pinocembrin (which is the active component of propolis) was prepared.

In order to prevent the multifilament from being degraded by water when the multifilament is impregnated with the grapefruit seed extract and the active component of propolis, methanol having a high degree of evaporation was used as a solvent for dissolving the grapefruit seed extract and the active component of propolis.

Figure 4A:
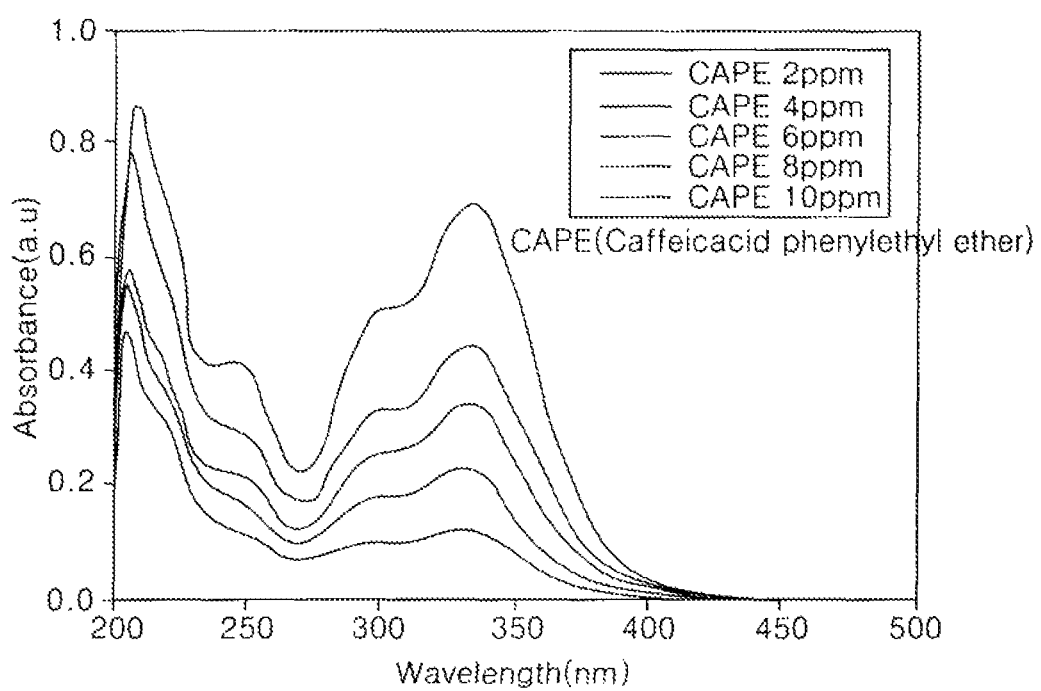
FIGS. 4A, 4B and 4C show the UV-Vis spectra of a grapefruit seed extract and an active component of propolis according to one embodiment of the present invention.
Figure 4B:
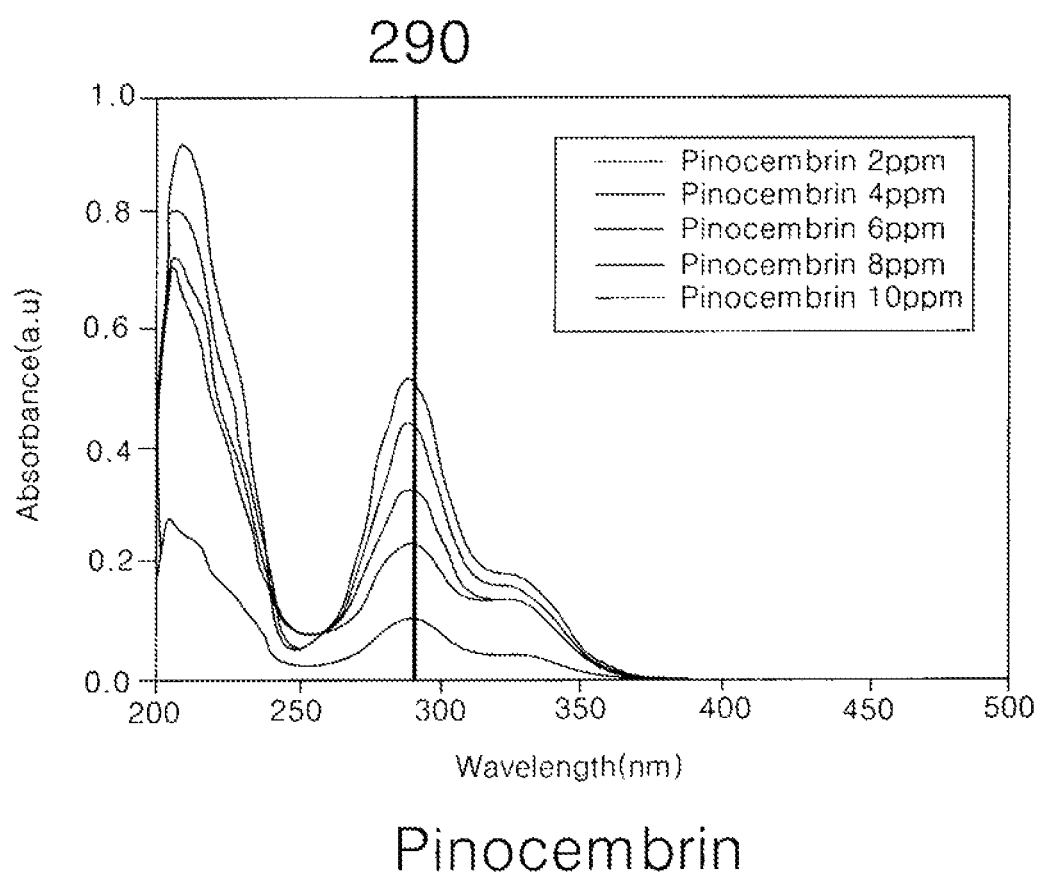
Figure 4C:
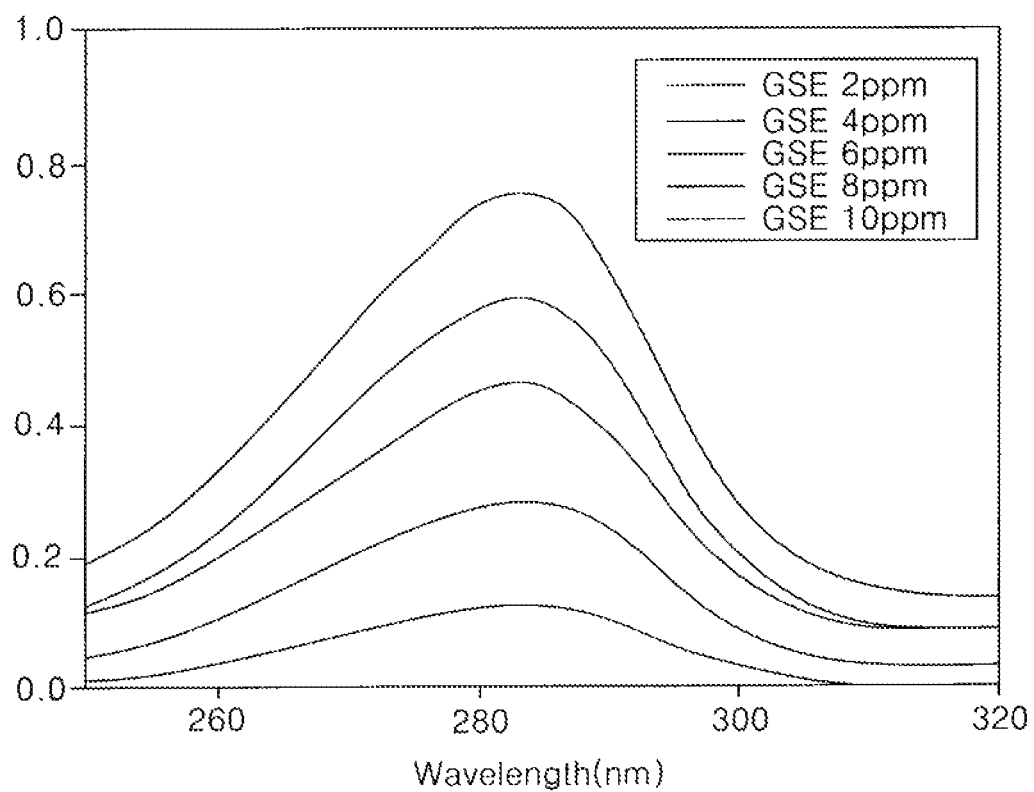

FIGS. 4A, 4B and 4C show the results of UV-Vis analysis conducted using JASCO V-550 UV-Vis Spectrophotometer (Wavelength Range: 200-900 nm, Bandwidth Selectable: 0.5 nm, Scanning Speed 400 nm/min, Data Pitch 1 nm) in order to examine the intrinsic wavelengths of the grapefruit seed extract, CAPE and pinocembrin. As can be seen therein, CAPE, pinocembrin and the grapefruit seed extract have intrinsic wavelengths of 330 nm, 290 nm and 283 nm, respectively.

EXAMPLE 3

Impregnation of the Multifilament with a Solution of the Grapefruit Seed Extract and the Active Component of Propolis 1 g of the multifilament prepared in Example 1 and 30 ml of the solution containing 1000 ppm of the grapefruit seed extract and CAPE or pinocembrin (the active component of propolis), prepared in Example 1, were placed in a vial and kept in the vial for 0, 80, 160, 240, 320, 400, 480, 540, 620, 680 and 1320 min. Then, the multifilament was taken out of the vial and dried in a vacuum.

In order to examine the absorption of the grapefruit seed extract and the active component of propolis in the multifilament, the remaining solution was analyzed by UV-Vis spectroscopy at wavelengths of 330 nm, 290 nm and 283 nm which are the wavelengths of CAPE and the grapefruit seed extract, thereby determining the contents of the grapefruit seed extract and the active components of propolis in the multifilament as a function of time. The results of the measurement are graphically shown in FIGS. 6A, 6B and 6C.

As can be seen in FIG. 6, for CAPE, the amount of loading became suitable at about 440 min, and for pinocembrin, the amount of loading became suitable at 720 min. For CAPE and GSE, the contents thereof in the multifilament reached the highest at about 440 min and no longer increased after 440 min. Thus, it could be seen that the time at which the impregnation of the grapefruit seed extract and the active components of propolis reached the maximum was 440 min. The sample at 440 min was used in the experiment.

EXAMPLE 4

Measurement of Drug Release

In order to examine the in vivo drug release of each of the multifilament samples impregnated with CAPE and GSE for 440 min and pinocembrin for 720 min in Example 3, the following test was performed.

As a solvent for use in this release test, 0.01M PBS (by phosphate buffer calculator, monobasic monohydrate: 1.1832 g, and dibasic ACS reagent: 8.1572 g) was prepared and adjusted to a pH of 7.4.

Figure 5A:
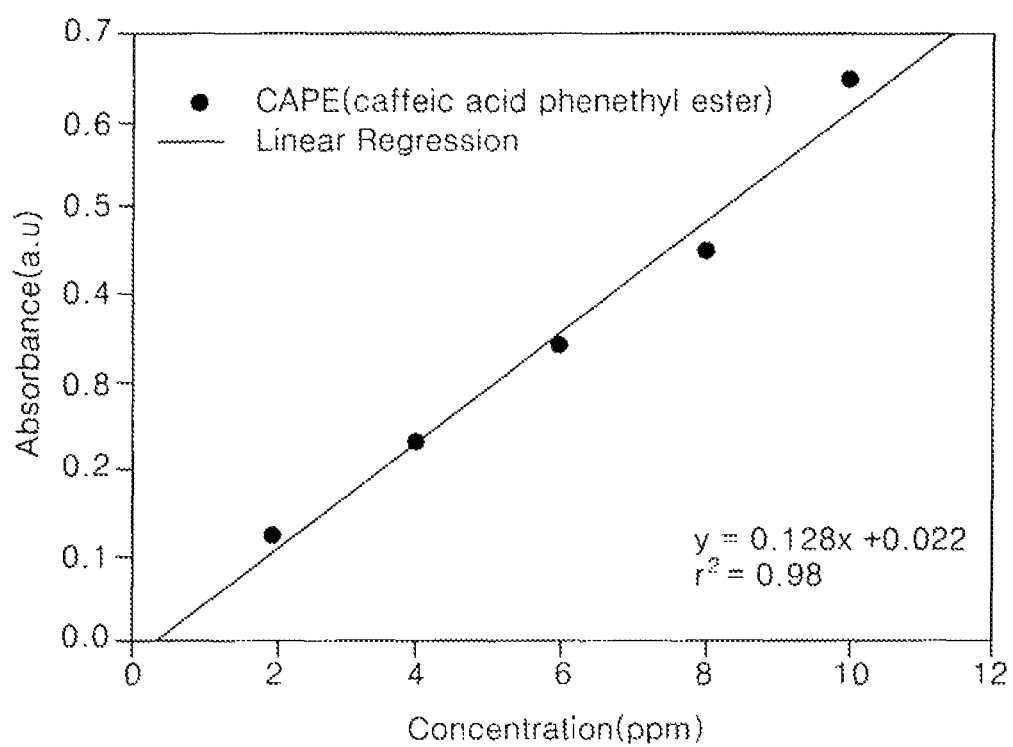
FIGS. 5A, 5B and 5C are standard curves of solutions of a grapefruit seed extract and an active component of propolis.
Figure 5B:
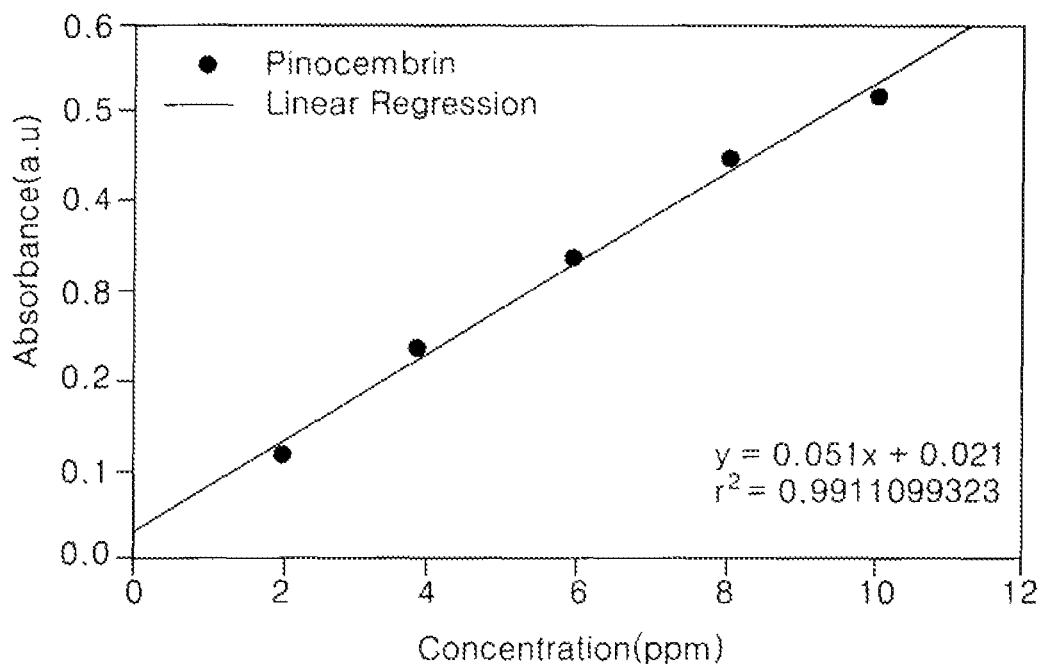
Figure 5C:
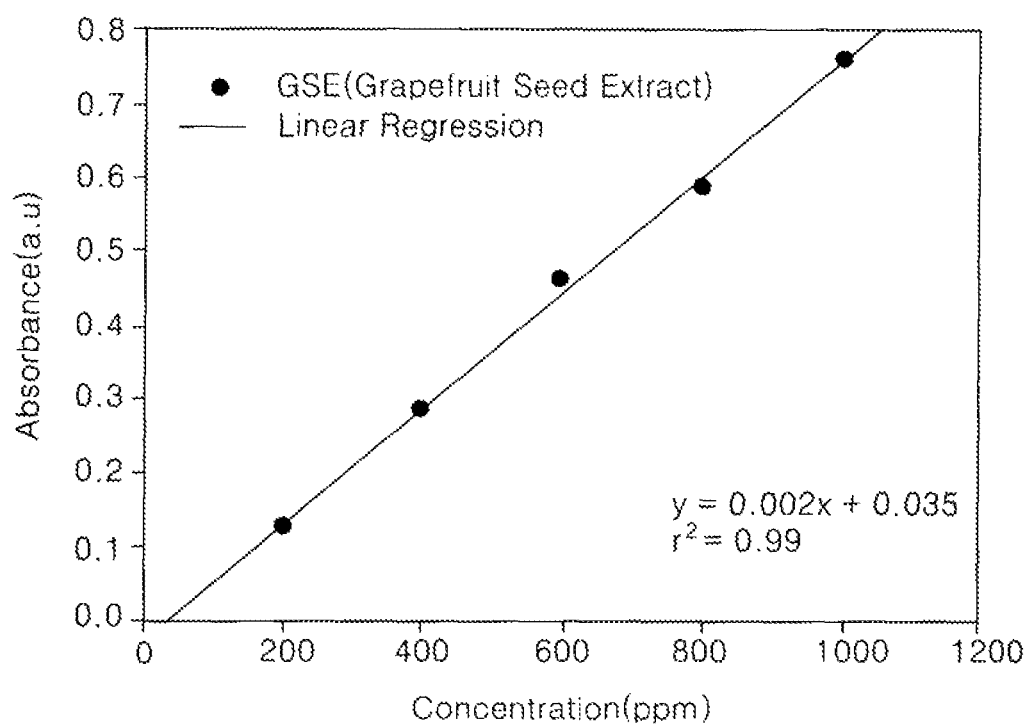

After standard curves of FIGS. 5A, 5B and 5C for the grapefruit seed extracts and CAPE and pinocembrin (the active components of propolis) were plotted, and then tests for the materials were performed at the respective concentrations. The standard curves for the functional materials were obtained by measuring the absorbance using JASCO V-550 UV-Vis Spectrometer (Wavelength Range: 200-900 nm; Bandwidth Selectable: 0.5 nm; Scanning Speed: 400 nm/min; Data Pitch: 1 nm). The standard curve equations shown in FIGS. 5A (CAPE), 5B (Pinocembrin) and 5C (grapefruit seed extract) are as follows:

$$y=0.126x+0.022 \quad \text{CAPE} \quad (1)$$

$$y=0.051x+0.021 \quad \text{Pinocembrin} \quad (2)$$

$$y=0.002x-0.035 \quad \text{Grapefruit seed extract} \quad (3)$$

wherein x is the concentration of each functional material, and y is the absorbance of each functional material.

1 g of the multifilament was impregnated with 30 ml of a solution containing 1000 ppm of the grapefruit seed extract and CAPE and pinocembrin (which are the active components of propolis) with stirring for 440 min, followed by filtration. The filtered multifilament was dried and 5 mL of 0.01M PBS was added to 1 g of the dried multifilament using a pipette. Each of the samples was placed in a shaker, and 5 ml of each sample was extracted using a pipette at 6-hr intervals for 100 hours. Then, 5 mL of PBS was placed in the shaker, and the internal temperature of the shaker was adjusted to 37 similar to the body temperature.

Figure 7A:
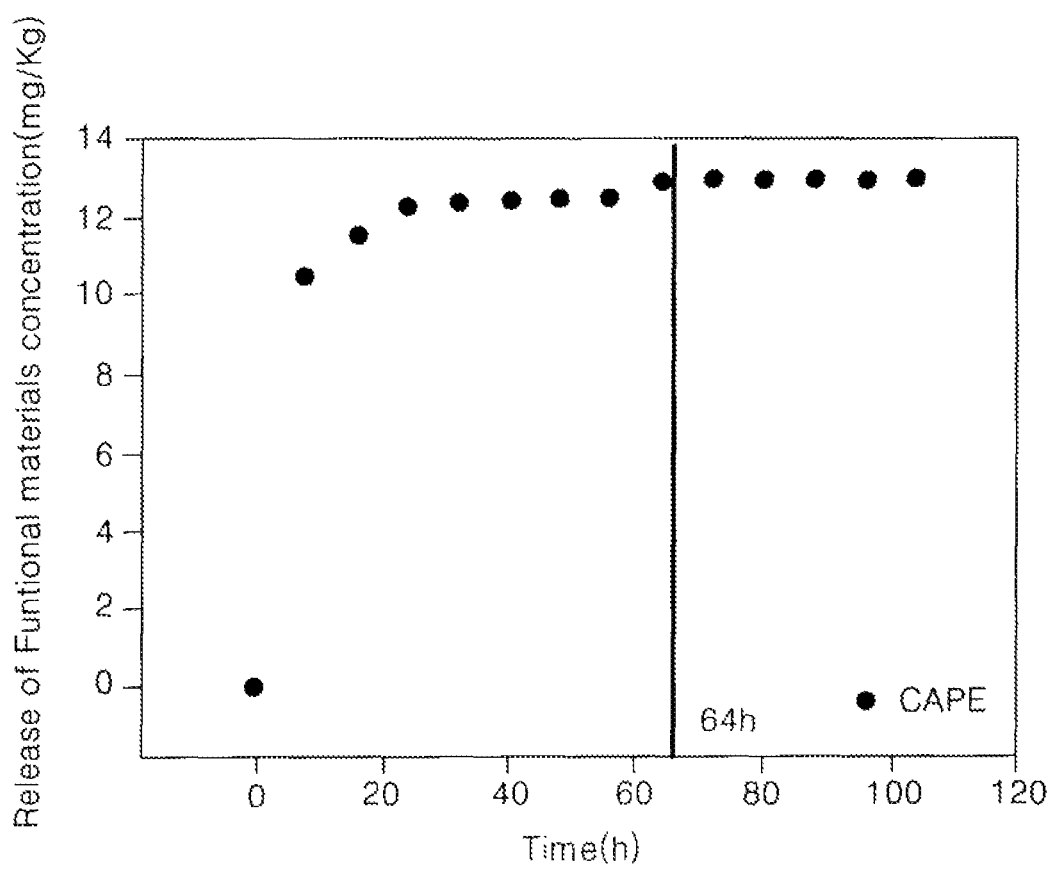
FIGS. 7A, 7B and 7C show the results of measuring the drug release of a medical product containing a grapefruit seed extract and an active component of propolis and are graphs showing the concentration (ppm) of the grapefruit seed extract and the active component of propolis as a function of time.
Figure 7B:
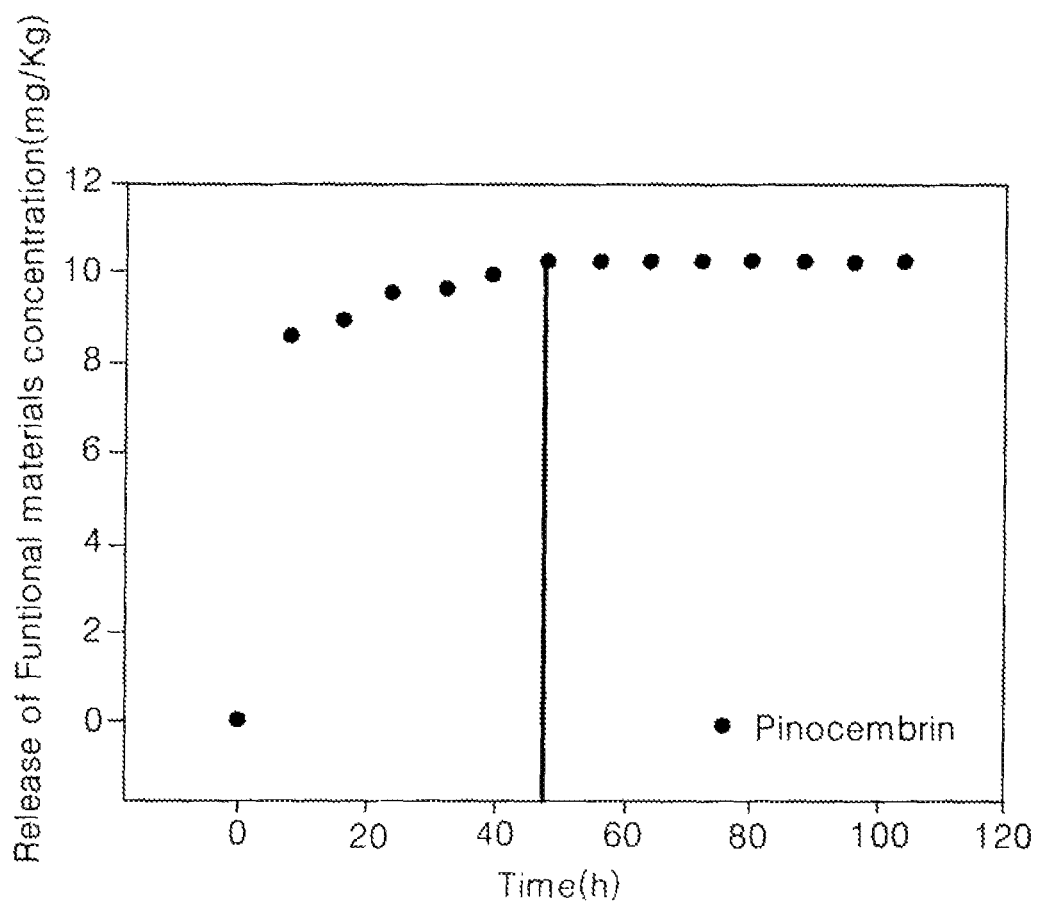
Figure 7C:
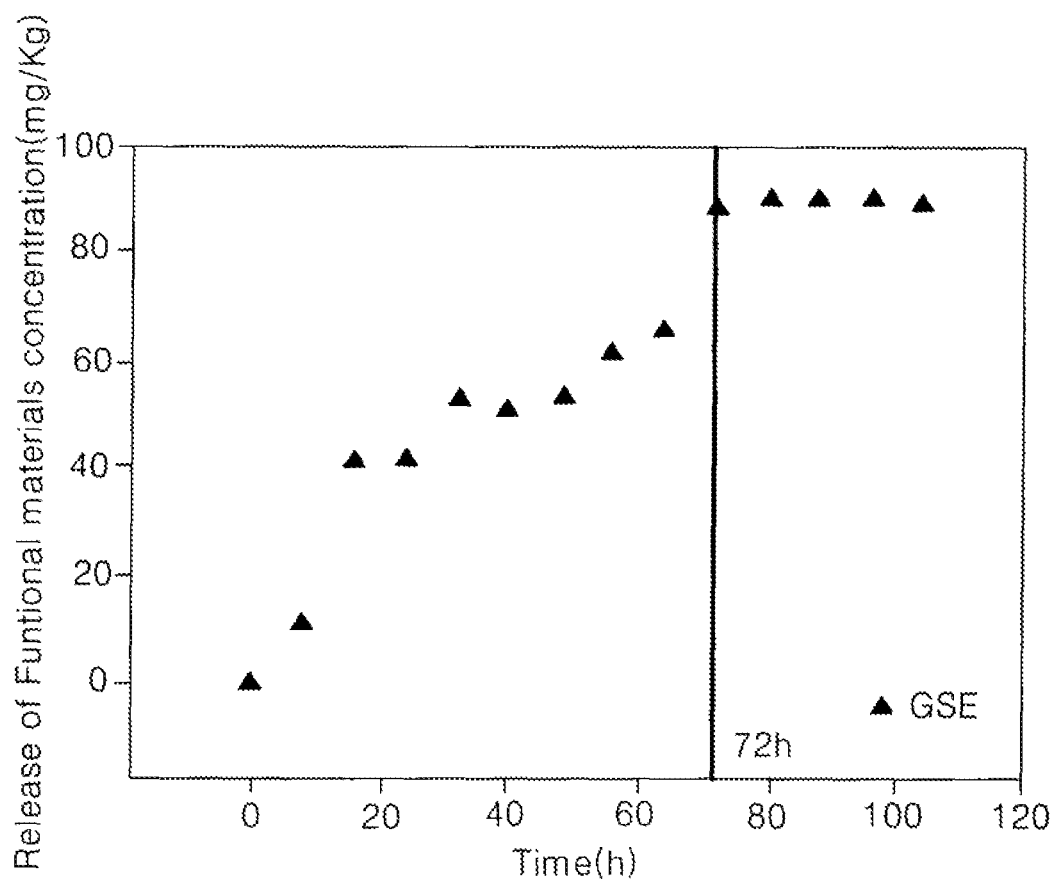

FIG. 7 show the release profiles of the grapefruit seed extracts and the active components (CAPE and Pinocembrin) of propolis in the multifilament and indicate the time at which the functional materials are released in vivo.

In the test, the drug release of the multifilament samples containing the grapefruit seed extract and the active components of propolis was examined for 0-100 hours. As a result, in the environment similar to the body, the drug release behavior was completed within about 64 hours for CAPE, about 60 hours for pinocembrin, and about 72 hours for the grapefruit seed extract. This suggests that the antibacterial and anti-inflammatory activities of the multifilament introduced in vivo are maintained for about 2-3 days, thus reducing infection caused by the bacteria of the multifilament in vivo before and after surgery.

EXAMPLE 5

Antibacterial Activity

The antibacterial activity of the multifilament of Example containing the grapefruit seed extract and the active components (CAPE and pinocembrin) of propolis was tested.

In the test, the cells of bacterial strains were grown in LB medium (peptone 10 g) by agar diffusion, and the growth of the bacterial strains was examined by UV-Vis spectroscopy. As the test strains, *Staphylococcus aureus* (ATCC 6538) and *Escherichia coli* DH 5α (ATCC 25922) were used. The bacterial cells were cultured at 37.1° C. for 24 hours, and then changes in the bacterial strains were measured.

Figure 6A:
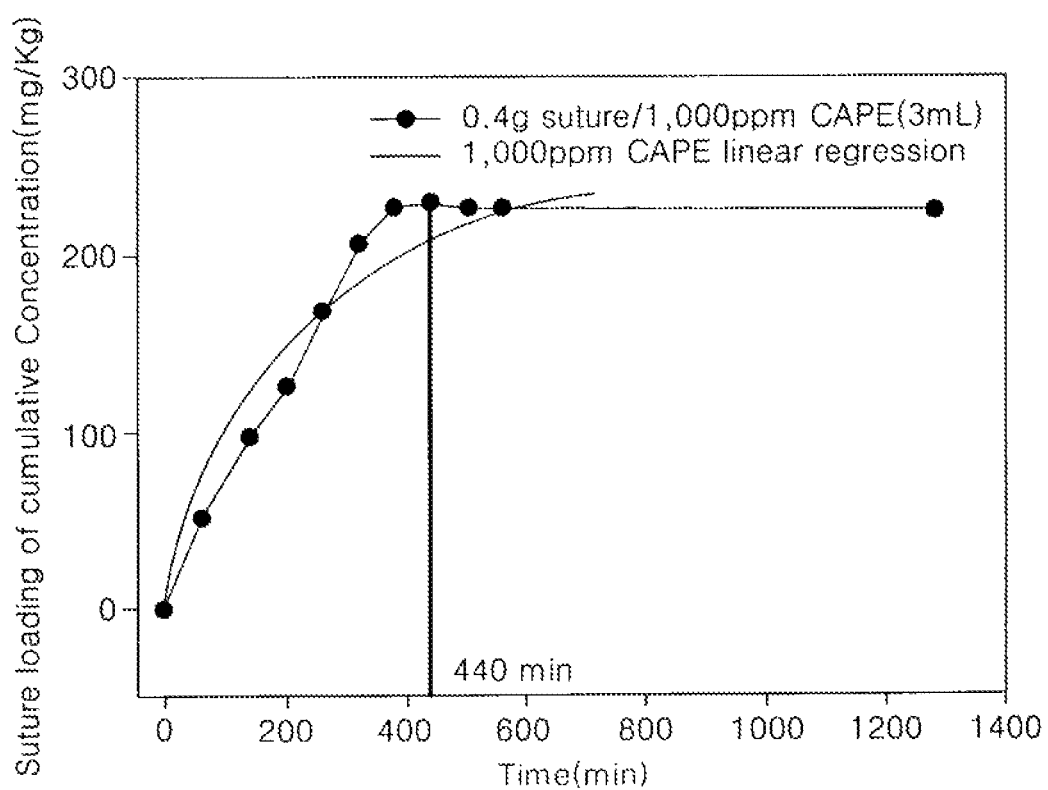
FIGS. 6A, 6B and 6C are graphs showing the loading of a medical product containing 1000 ppm of a grapefruit seed extract and an active component of propolis according to one embodiment of the present invention.
Figure 6B:
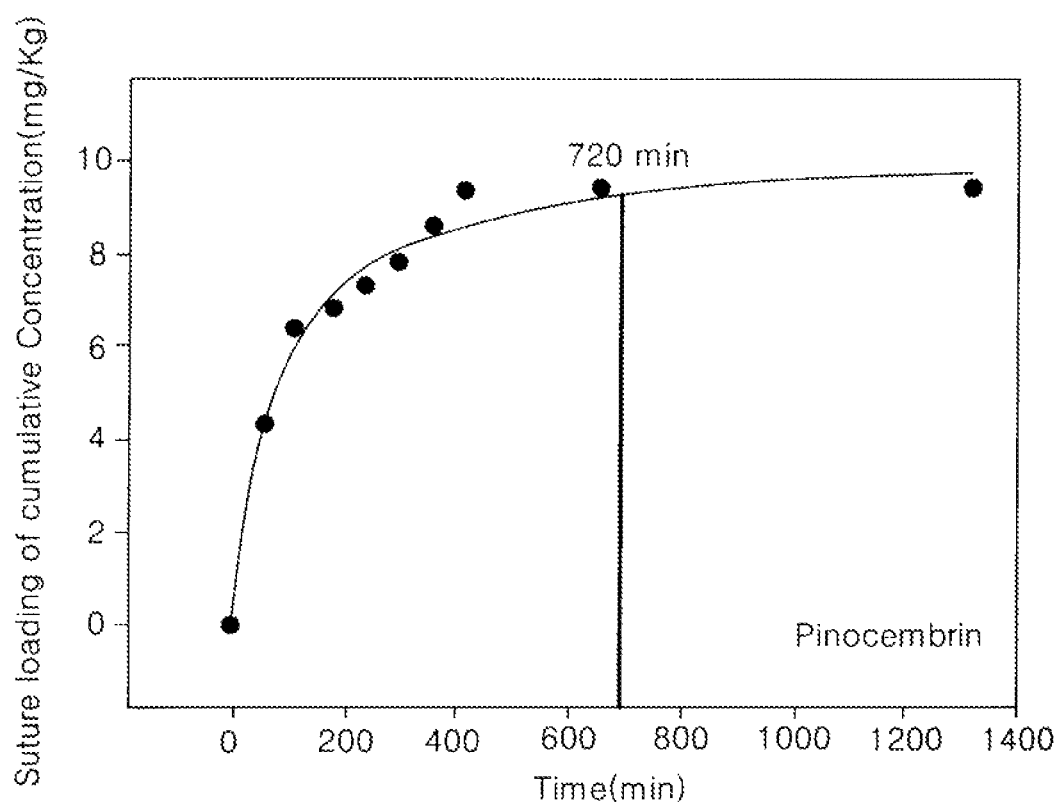
Figure 6C:
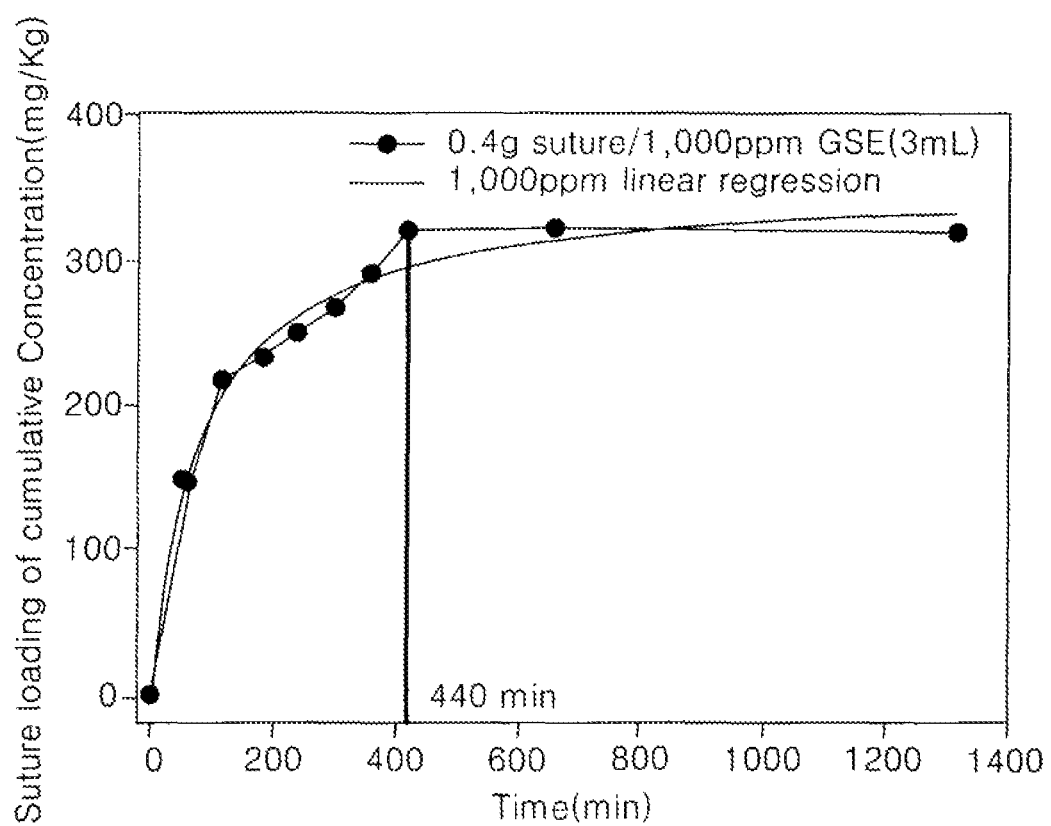
Figure 8:
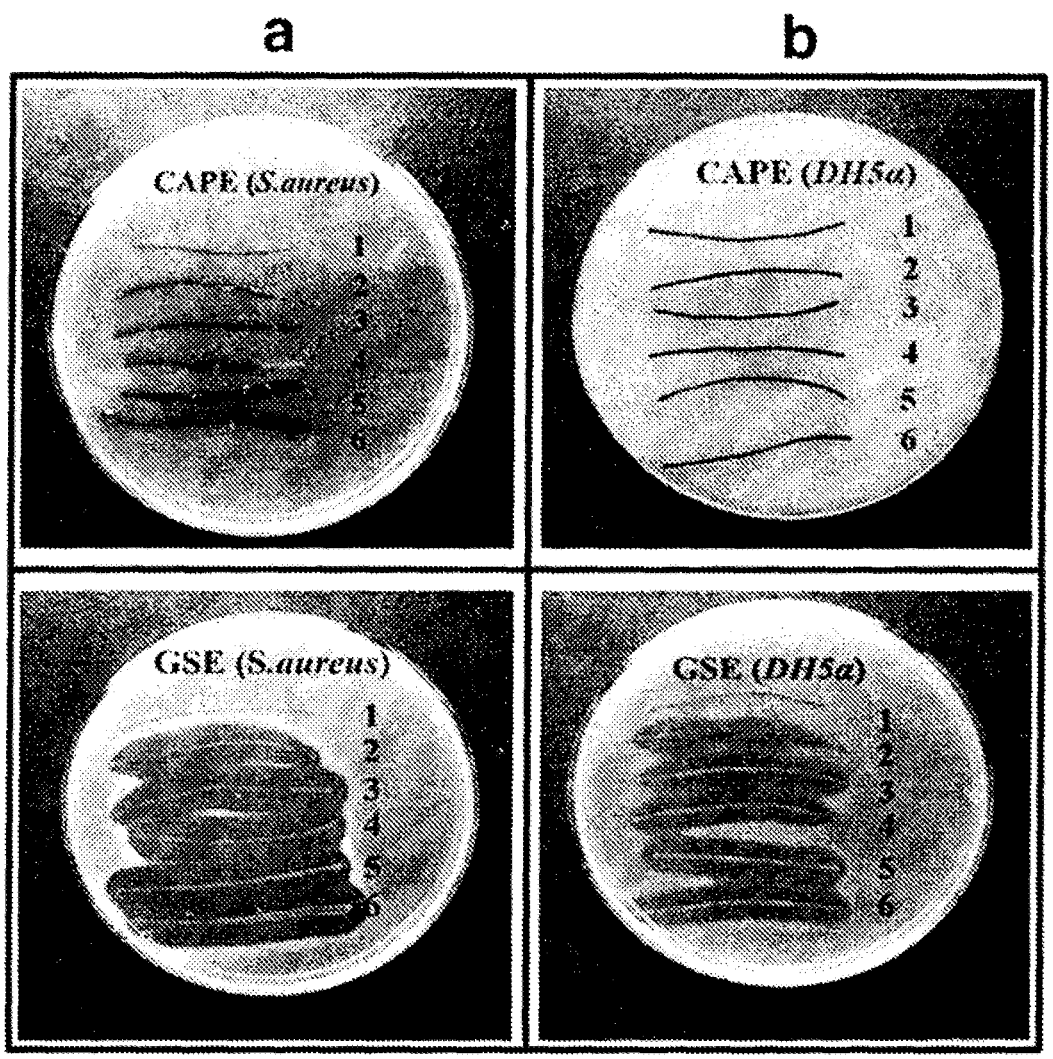
FIG. 8 shows the results of measuring the antibacterial activity of a multifilament (for a medical product) containing a grapefruit seed extract and an active component of propolis according to one embodiment of the present invention.

FIG. 8 is a set of photographs showing a comparison of antibacterial activity between a multifilament containing the grapefruit seed extract and a multifilament containing the active component (CAPE) of propolis. In FIG. 8, antibacterial activities against the two bacterial strains can be seen and it can be seen that the grapefruit seed extract and the active component (CAPE) of propolis, which were contained in the multifilament, showed different antibacterial activities. In FIG. 8, 1: a control group, 2 to 6: samples impregnated with a solution of CAPE and the grapefruit seed extract; a: a sample treated with *Staphylococcus aureus*; b: a sample treated with *Escherichia coli* DH 5α. In the photograph of FIG. 8, the treatment concentration is 1000 ppm. As can be seen in FIGS. 6A, 6B and 6C, a concentration of 1000 ppm is not completely contained in the medical product, and for this reason, it is believed that the medical product contains a lower concentration of the functional material and that an inflammatory response caused by a high concentration of the functional material can be avoided. Also, when the multifilament before treatment with the antibacterial material is compared with the multifilament impregnated with the antibacterial material, it could be seen that clear antibacterial activity was expressed and that the two antibacterial materials all showed antibacterial activity. Although a lower concentration of the antibacterial material is contained in the multifilament, it is considered that the test should be carried out at 1000 ppm, because the concentration of the antibacterial material in the multifilament will be excessively low when the test is carried out at a lower concentration. Also, subsequent tests were all carried out at 1000 ppm.

Also important is the difference in antibacterial activity between *Staphylococcus aureus* and *E. coli*. This difference results from merely the difference in cell wall thickness between gram-positive *Staphylococcus aureus* and gram-negative *E. coli*, thus both of them show the suitable antibacterial activity.

Particularly, when the grapefruit seed extract was tested in the same amount as that of CAPE, the grapefruit seed extract had higher antibacterial activity than CAPE, suggesting that the grapefruit seed extract and CAPE had antibacterial activity. However, the grapefruit seed extract is comprised of a mixture of flavonoids, whereas CAPE which is the active component of propolis is a single material. Thus, it is unreasonable to compare the antibacterial activity between the two functional materials. Thus, it is significant that the two functional materials have antibacterial activity.

As described above, the medical antibacterial product of the present invention comprises the multifilament containing contains the grapefruit seed extract and CAPE and pinocembrin (which are the active components of propolis) having antibacterial and anti-inflammatory effects, in which the grapefruit seed extract and CAPE and pinocembrin can impart antibacterial and anti-inflammatory functions to the medical product so as to prevent pathogenic infection from occurring due to the medical product. That is, the grapefruit seed extract and CAPE and pinocembrin can improve the sanitation of the medical product, prevent the occurrence of fungi on the surface of the medical product that is the main cause of the secondary infection during surgery, and may stably maintain the strength and tension of the medical product.

As described above, according to the present invention, the grapefruit seed extract and the active component of propolis which have antibacterial and anti-inflammatory effects are contained in the medical product, whereby they can impart antibacterial and anti-inflammatory functions to the medical product so as to prevent pathogenic infection from occurring due to the medical product.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A method for manufacturing a multifilament medical product which is an absorbent cotton wool, a bandage, a cotton gauze or cotton wool swab, the method comprising:
   preparing a solution by dissolving a grapefruit seed extract, and CAPE (caffeic acid phenyl ester) and pinocembrin, in which the concentration of each component is 1000 ppm, in methanol;
   impregnating a multifilament medical product for 440 minutes with the solution; and
   dehydrating the impregnated multifilament under vacuum conditions.

* * * * *